(12) United States Patent
Dirksen

(10) Patent No.: US 10,092,270 B2
(45) Date of Patent: Oct. 9, 2018

(54) PRE-COLLAPSED CMUT WITH MECHANICAL COLLAPSE RETENTION

(75) Inventor: Peter Dirksen, Valkenswaard (NL)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 316 days.

(21) Appl. No.: 13/203,751

(22) PCT Filed: Feb. 10, 2010

(86) PCT No.: PCT/IB2010/050614
§ 371 (c)(1),
(2), (4) Date: Sep. 26, 2011

(87) PCT Pub. No.: WO2010/097729
PCT Pub. Date: Sep. 2, 2010

(65) Prior Publication Data
US 2012/0010538 A1    Jan. 12, 2012

Related U.S. Application Data

(63) Continuation-in-part of application No. 12/678,453, filed as application No. PCT/IB2008/053778 on Sep. 17, 2008, now Pat. No. 8,327,521.

(60) Provisional application No. 61/155,988, filed on Feb. 27, 2009, provisional application No. 60/972,836, filed on Sep. 17, 2007.

(51) Int. Cl.
*A61H 1/00* (2006.01)
*A61B 8/00* (2006.01)
*B06B 1/02* (2006.01)

(52) U.S. Cl.
CPC .............. *A61B 8/00* (2013.01); *A61B 8/4483* (2013.01); *B06B 1/0292* (2013.01)

(58) Field of Classification Search
CPC .............................. A61N 7/00; A61H 23/0245
USPC .............................................................. 601/2
See application file for complete search history.

(56) References Cited

U.S. PATENT DOCUMENTS

| 3,993,939 A | 11/1976 | Slavin et al. |
| 4,437,468 A | 3/1984 | Sorenson et al. |
| 5,152,294 A | 10/1992 | Mochizuki et al. |
| 5,159,931 A | 11/1992 | Pini |

(Continued)

FOREIGN PATENT DOCUMENTS

| EP | 0133007 A | 2/1985 |
| EP | 0707318 A | 4/1996 |

(Continued)

OTHER PUBLICATIONS

"Capacitive Micromachined Ultrasonic Transducers: Fabrication Technology" Ergun et al, IEEE Transactions on Ultrasonics . . . , vol. 52, No. 12, Dec. 2005 p. 2242-2258.

*Primary Examiner* — Hien Nguyen

(57) ABSTRACT

A CMUT transducer cell suitable for use in an ultrasonic CMUT transducer array has a membrane with a first electrode, a substrate with a second electrode, and a cavity between the membrane and the substrate. The CMUT is operated in a precollapsed state by biasing the membrane to a collapsed condition with the floor of the cavity, and a lens is cast over the collapsed membrane. When the lens material has polymerized or is of a sufficient stiffness, the bias voltage is removed and the lens material retains the membrane in the collapsed state.

20 Claims, 6 Drawing Sheets

(56) References Cited

U.S. PATENT DOCUMENTS

| | | |
|---|---|---|
| 5,460,179 A | 10/1995 | Okunuki et al. |
| 5,997,479 A | 12/1999 | Savord et al. |
| 6,572,548 B2 | 6/2003 | Cerofolini |
| 6,632,178 B1 | 10/2003 | Fraser |
| 2003/0018269 A1 | 1/2003 | Angelsen et al. |
| 2003/0229286 A1 | 12/2003 | Lenker |
| 2005/0075572 A1* | 4/2005 | Mills et al. .................. 600/459 |
| 2005/0146247 A1* | 7/2005 | Fisher et al. ................. 310/334 |
| 2005/0200241 A1 | 9/2005 | Degertekin |
| 2007/0194658 A1* | 8/2007 | Zhang et al. ................. 310/314 |
| 2008/0064959 A1* | 3/2008 | Kanda ................ G01S 7/52023 600/459 |
| 2008/0089180 A1* | 4/2008 | Matsumoto et al. ......... 367/181 |
| 2010/0036257 A1* | 2/2010 | Sano .................... A61B 8/4281 600/459 |
| 2011/0071396 A1* | 3/2011 | Sano .................... A61B 8/4455 600/443 |

FOREIGN PATENT DOCUMENTS

| | | |
|---|---|---|
| WO | 2005094690 A1 | 10/2005 |
| WO | 2005096266 A | 10/2005 |
| WO | 2009016606 A2 | 2/2009 |
| WO | 2009037655 A2 | 3/2009 |

\* cited by examiner

PRE-COLLAPSED CMUT WITH MECHANICAL COLLAPSE RETENTION

This application is a national stage entry of international patent application no. PCT/IB10/50614 filed Feb. 10, 2010 which claims the benefit of U.S. provisional application no. 61/155,988 filed Feb. 27, 2009; this application is a continuation-in-part of U.S. patent application Ser. No. 12/678,453 filed Mar. 16, 2010, now U.S. Pat No. 8,327,521 which is a national stage entry of international application no. PCT/IB2008/053778, filed Sep. 17, 2008 which claims the benefit of U.S. provisional application no. 60/972,836, filed Sep. 17, 2007

This invention relates to medical diagnostic ultrasonic imaging and, in particular, to ultrasound probes which use capacitive micromachined ultrasonic transducers (CMUTs).

The ultrasonic transducers used for medical imaging have numerous characteristics which lead to the production of high quality diagnostic images. Among these are broad bandwidth and high sensitivity to low level acoustic signals at ultrasonic frequencies. Conventionally the piezoelectric materials which possess these characteristics and thus have been used for ultrasonic transducers have been made of PZT and PVDF materials, with PZT being the most preferred. However the ceramic PZT materials require manufacturing processes including dicing, matching layer bonding, fillers, electroplating and interconnections which are distinctly different and complex and require extensive handling, all of which can result in transducer stack unit yields which are less than desired. Furthermore, this manufacturing complexity increases the cost of the final transducer probe. As ultrasound system mainframes have become smaller and dominated by field programmable gate arrays (FPGAs) and software for much of the signal processing functionality, the cost of system mainframes has dropped with the size of the systems. Ultrasound systems are now available in inexpensive portable, desktop and handheld form. As a result, the cost of the transducer probe is an ever-increasing percentage of the overall cost of the system, an increase which has been accelerated by the advent of higher element-count arrays used for 3D imaging. Accordingly it is desirable to be able to manufacture transducer arrays with improved yields and at lower cost to facilitate the need for low-cost ultrasound systems.

Recent developments have led to the prospect that medical ultrasound transducers can be manufactured by semiconductor processes. Desirably these processes should be the same ones used to produce the circuitry needed by an ultrasound probe such as a CMOS process. These developments have produced micromachined ultrasonic transducers or MUTs. MUTs have been fabricated in two design approaches, one using a semiconductor layer with piezoelectric properties (PMUTs) and another using a diaphragm and substrate with electrode plates that exhibit a capacitive effect (CMUTs). The CMUT transducers are tiny diaphragm-like devices with electrodes that convert the sound vibration of a received ultrasound signal into a modulated capacitance. For transmission the capacitive charge applied to the electrodes is modulated to vibrate the diaphragm of the device and thereby transmit a sound wave. Since these devices are manufactured by semiconductor processes the devices generally have dimensions in the 10-200 micron range, but can range up to device diameters of 300-500 microns. Many such individual CMUTs can be connected together and operated in unison as a single transducer element. For example, four to sixteen CMUTs can be coupled together to function in unison as a single transducer element. A typical 2D transducer array currently will have 2000-3000 piezoelectric transducer elements. When fabricated as a CMUT array, over one million CMUT cells will be used. Surprisingly, early results have indicated that the yields on semiconductor fab CMUT arrays of this size should be markedly improved over the yields for PZT arrays of several thousand transducer elements.

CMUTs were initially produced to operate in what is now known as an "uncollapsed" mode. Referring to FIG. 1, a typical uncollapsed CMUT transducer cell 10 is shown in cross-section. The CMUT transducer cell 10 is fabricated along with a plurality of similar adjacent cells on a substrate 12 such as silicon. A diaphragm or membrane 14 which may be made of silicon nitride is supported above the substrate by an insulating support 16 which may be made of silicon oxide or silicon nitride. The cavity 18 between the membrane and the substrate may be air or gas-filled or wholly or partially evacuated. A conductive film or layer 20 such as gold forms an electrode on the diaphragm, and a similar film or layer 22 forms an electrode on the substrate. These two electrodes, separated by the dielectric cavity 18, form a capacitance. When an acoustic signal causes the membrane 14 to vibrate the variation in the capacitance can be detected, thereby transducing the acoustic wave into a corresponding electrical signal. Conversely, an a.c. signal applied to the electrodes 20,22 will modulate the capacitance, causing the membrane to move and thereby transmit an acoustic signal.

Due to the micron-size dimensions of a typical CMUT, numerous CMUT cells are typically fabricated in close proximity to form a single transducer element. The individual cells can have round, rectangular, hexagonal, or other peripheral shapes. FIG. 3 is a topographical image produced by an optical interferometer of a circular CMUT cell of the present invention. FIG. 4 is an interferometric image of an array of circular CMUT cells. The CMUT cells can have different dimensions so that a transducer element will have composite characteristics of the different cell sizes, giving the transducer a broad band characteristic. Generally such cell size differentiation is not necessary, as most CMUTs normally have a bandwidth of 100% or more of the applied signal bandwidth.

The CMUT is inherently a quadratic device so that the acoustic signal is normally the harmonic of the applied signal, that is, the acoustic signal will be at twice the frequency of the applied electrical signal frequency. To prevent this quadratic behavior a bias voltage is applied to the two electrodes which causes the diaphragm to be attracted to the substrate by the resulting coulombic force. This is shown schematically in FIG. 2, where a DC bias voltage $V_B$ is applied to a bias terminal 24 and is coupled to the membrane electrode 20 by a path which poses a high impedance Z to a.c. signals such as an inductive impedance. A.c. signals are capacitively coupled to and from the membrane electrode from a signal terminal 26. The positive charge on the membrane 14 causes the membrane to distend as it is attracted to the negative charge on the substrate 12. The CMUT cell only weakly exhibits the quadratic behavior when operated continuously in this biased state.

It has been found that the CMUT is most sensitive when the membrane is distended so that the two oppositely charged plates of the capacitive device are as close together as possible. A close proximity of the two plates will cause a greater coupling between acoustic and electrical signal energy by the CMUT. Thus it is desirable to increase the bias voltage $V_B$ until the dielectric spacing 32 between the membrane 14 and substrate 12 is as small as can be maintained under operating signal conditions. In constructed embodiments this spacing has been on the order of one micron or less. If the applied bias voltage is too great, however, the membrane can contact the substrate, short-circuiting the device as the two plates of the device are stuck together by VanderWals forces. This sticking can occur when the CMUT cell is overdriven, and can vary from one device to another with the same bias voltage $V_B$ due to manufacturing tolerance variations. While permanent sticking can be reduced be embedding the device electrodes in an electrical isolation layer (e.g., silicon nitride), the nonlinearity of operation between collapsed and uncollapsed states is an inherent disadvantage when trying to operate an uncollapsed CMUT in a range of maximal sensitivity.

Even when the membrane is biased to cause a very small sub-micron dielectric spacing, the sensitivity of the CMUT can be less than that which is desired. This is due to the fact that, whereas the charge at the center 32 of the membrane is relatively close to and will move considerably in relation to the opposing charge, the charge at the periphery 34 of the membrane where the membrane is supported by the support 16 will move very little and hence have little participation in the transduction of signals by the device. One approach to eliminating this disparity has been to use a small membrane electrode 20 which does not extend to the supports 16. This restricts the charge on the membrane electrode to the center of the device where it will participate strongly in the motion of the membrane and hence the transduction by the device. There still must be one or more electrical conductors to apply the bias voltage $V_B$ to the membrane electrode 20 and to couple the a.c. signals to and from the electrode. These electrical conductors are necessarily very thin, with dimensions that impose undesirably large impedances on the a.c. signals, thereby limiting the sensitivity of the device.

It is an object of the present invention to provide a CMUT transducer cell with good sensitivity but which is immune to the membrane sticking problem.

It is a further object of the present invention to provide a CMUT transducer cell which can be maintained in an efficient range of operation with a low bias voltage.

It is a further object of the present invention to provide a CMUT transducer cell which operates consistently from lot to lot in the presence of anticipated manufacturing tolerances.

It is a further object of the present invention to provide a CMUT transducer array which can be fabricated with semiconductor processes that are compatible with those of the integrated circuitry used to operate the array such as a CMOS process.

In accordance with the principles of the present invention, an ultrasonic transducer CMUT cell array is provided which operates in the "precollapsed" mode. In the precollapsed mode the sticking problem is avoided because the membrane is continually in contact with the floor of the cavity of the CMUT cell. Hysteresis is avoided by use of a range of operation which does not switch between uncollapsed and precollapsed states and continually operating in the precollapsed mode. The bias voltage conventionally needed to maintain the membrane in the precollapsed mode is replaced by a mechanical structure which physically maintains the collapsed condition of the membrane. This enables the CMUT to operate in a favorable range of operation with low operating and bias voltages. In a preferred embodiment the mechanical structure which maintains the CMUT cell in the collapsed condition is a lens of the ultrasonic transducer array.

Figure 3:
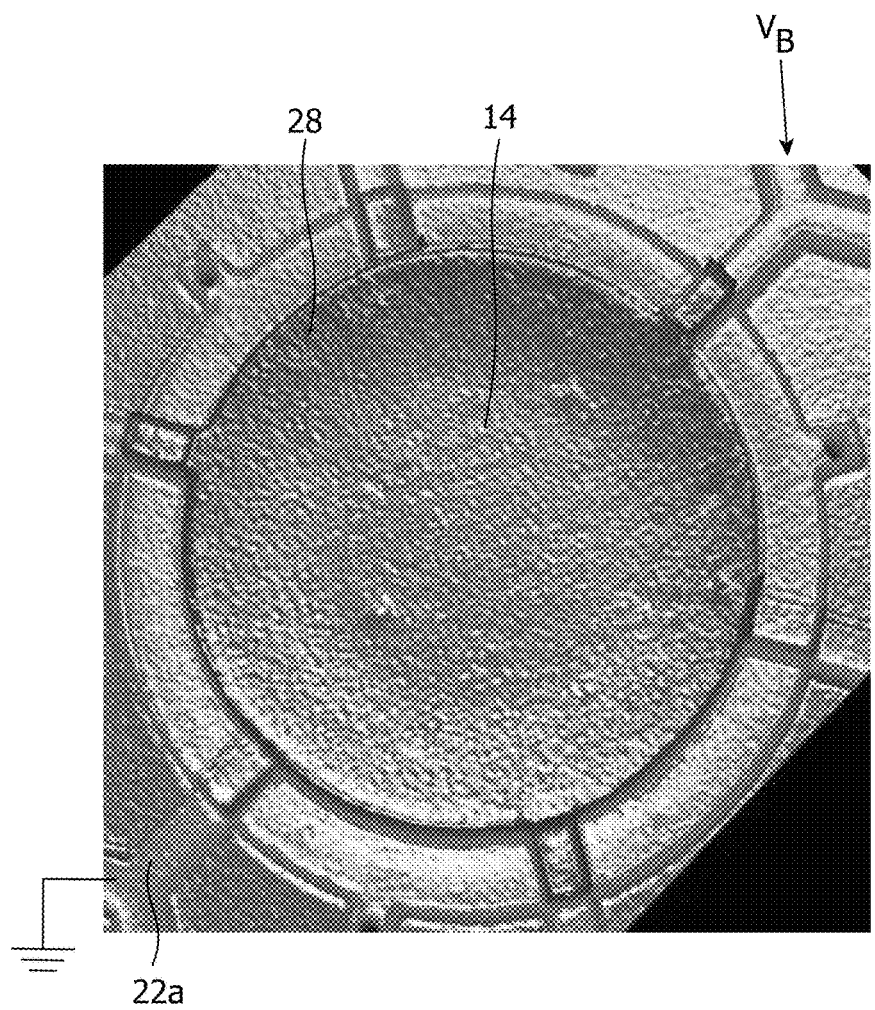
FIG. 3 is a topographical interferometric image of a CMUT cell of the present invention.
Figure 4:
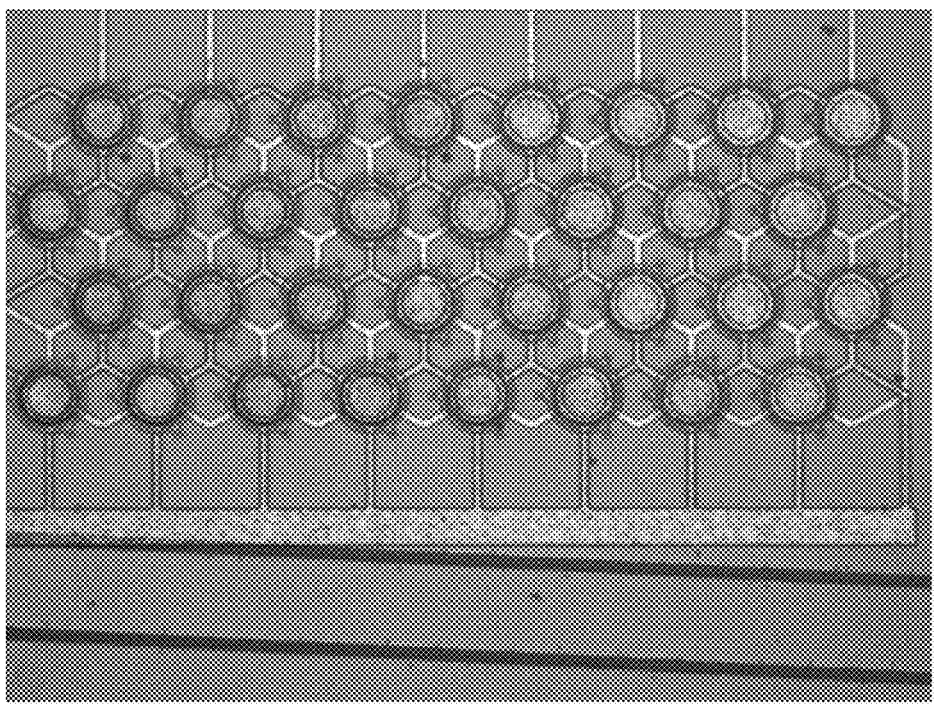
FIG. 4 is an interferometric image of an array of circular CMUT cells.
Figure 5:
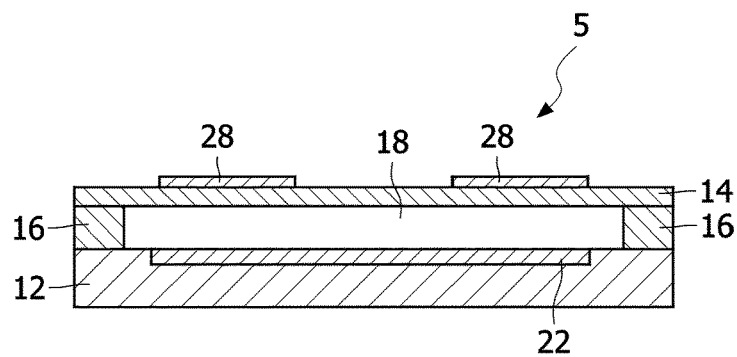
FIG. 5 is a cross-sectional view of a CMUT cell constructed in accordance with the principles of the present invention.

With reference to FIG. 5, a schematic cross-section of a CMUT element 5 is depicted. CMUT element 5 includes a substrate layer 12, an electrode 22, a membrane layer 14, and a membrane electrode ring 28, the circular form of which is seen in FIGS. 3 and 4. In this example, the electrode 22 is circularly configured and embedded in the substrate layer 12. In addition, the membrane layer 14 is fixed relative to the top face of the substrate layer 12 and configured/dimensioned so as to define a spherical or cylindrical cavity 18 between the membrane layer 14 and the substrate layer 12. As previously mentioned, the cell and its cavity 18 may define alternative geometries. For example, cavity 18 could define a rectangular and/or square cross-section, a hexagonal cross-section, an elliptical cross-section, or an irregular cross-section.

The bottom electrode 22 is typically insulated on its cavity-facing surface with an additional layer (not pictured). A preferred insulating layer is an oxide-nitride-oxide (ONO) dielectric layer formed above the substrate electrode and below the membrane electrode. The ONO-dielectric layer advantageously reduced charge accumulation on the electrodes which leads to device instability and drift and reduction in acoustic output pressure. The fabrication of ONO-dielectric layers on a CMUT is discussed in detail in European patent application no. 08305553.3 by Klootwijk et al., filed Sep. 16, 2008 and entitled "Capacitive micromachined ultrasound transducer." Use of the ONO-dielectric layer is desirable with precollapsed CMUT, which are more susceptible to charge retention than are uncollapsed device. The disclosed components may be fabricated from CMOS compatible materials, e.g., Al, Ti, nitrides (e.g., silicon nitride), oxides (various grades), tetra ethyl oxysilane (TEOS), poly-silicon and the like. In a CMOS fab, for example, the oxide and nitride layers may be formed by chemical vapor deposition and the metallization (electrode) layer put down by a sputtering process. Suitable CMOS processes are LPCVD and PECVD, the latter having a relatively low operating temperature of less than 400° C.

Exemplary techniques for producing the disclosed cavity 18 involve defining the cavity in an initial portion of the membrane layer 14 before adding a top face of the membrane layer 14. Other fabrication details may be found in U.S. Pat. No. 6,328,697 (Fraser). In the exemplary embodiment depicted in FIG. 5, the diameter of the cylindrical cavity 18 is larger than the diameter of the circularly configured electrode plate 22. Electrode ring 28 may have the same outer diameter as the circularly configured electrode plate 22, although such conformance is not required. Thus, in an exemplary embodiment of the present invention, the electrode ring 28 is fixed relative to the top face of the membrane layer 14 so as to align with the electrode plate 22 below.

Figure 6:
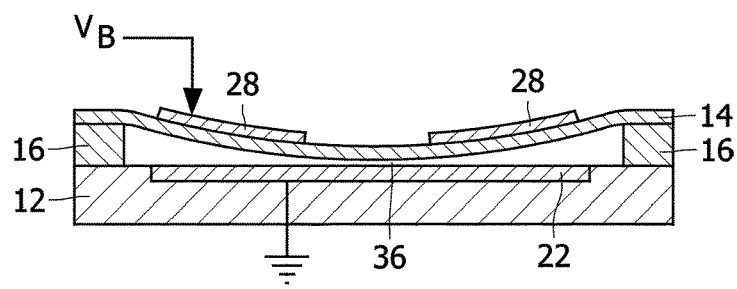
FIG. 6 illustrates the CMUT cell of FIG. 5 when biased into a collapsed state.

FIG. 6 shows the CMUT cell of FIG. 5 when biased to a precollapsed state, in which the membrane 14 is in contact with the floor of the cavity 18. This is accomplished by applying a DC bias voltage to the two electrodes as indicated by voltage $V_B$ applied to the electrode ring 28 and a reference potential (ground) applied to the substrate electrode 22. While the electrode ring 28 could also be formed as a continuous disk without the hole in the center, FIG. 6 illustrates why this is not necessary. When the membrane 14 is biased to its precollapsed state as shown in this drawing, the center of the membrane is in contact with the floor of the cavity 18. As such, the center of the membrane 14 does not move during operation of the CMUT. Rather, it is the peripheral area of the membrane 14 which moves, that which is above the remaining open void of the cavity 18 and below the ring electrode. By forming the membrane electrode 28 as a ring, the charge of the upper plate of the capacitance of the device is located above the area of the CMUT which exhibits the motion and capacitive variation when the CMUT is operating as a transducer. Thus, the coupling coefficient of the CMUT transducer is improved.

The membrane 14 may be brought to its precollapsed state in contact with the floor of the cavity 18 as indicated at 36 by applying the necessary bias voltage, which is typically in the range of 50-100 volts. As the voltage is increased, the capacitance of the CMUT cell is monitored with a capacitance meter. A sudden change in the capacitance indicates that the membrane has collapsed to the floor of the cavity. The membrane can be biased downward until it just touches the floor of the cavity as indicated at 36, or can be biased further downward to increased collapse beyond that of minimal contact.

Another way to bring the membrane 14 to its precollapsed state is to apply pressure to the top of the membrane. When the cavity is formed in a partial or complete vacuum, it has been found that the application of atmospheric pressure of 1 Bar is sufficient to precollapse the membrane 14 to contact with the floor of the cavity 18. It is also possible to use a combination of pressure differential and bias voltage to controllably precollapse the membrane 14, which is effective with smaller devices that may have a high atmospheric collapse pressure (e.g., 10 Bar.)

Figure 7:
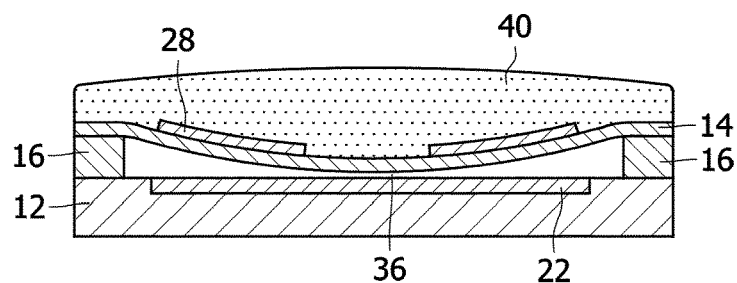
FIG. 7 illustrates the CMUT cell of FIG. 6 when the membrane is retained in the collapsed state by a lens fabricated on top of the cell.

In accordance with the principles of the present invention, while the membrane 14 is biased to its precollapsed state as shown in FIG. 6, a structure is placed or formed above the membrane which physically retains the membrane in its precollapsed state. In a preferred embodiment for an ultrasound transducer, the structure forms the lens 40 of the transducer. A transducer lens normally fulfills three requirements. One is that the lens provides a structure which endures wear resistance due to the frictional contact produced during use of the transducer probe. In effect, the lens provides a physical cover which protects the underlying transducer array from physical wear. Second, a lens is nonconductive and thereby provides electrical insulation between the electrical elements of the transducer and the patient. Third, a lens can provide focal properties for the probe. In the example of FIG. 7, the lens 40 provides a fourth benefit, which is to physically retain the membrane 14 in its precollapsed state.

Various materials may be used for the lens material. The only requirement for the CMUT is that the material be of sufficient stiffness to retain the membrane in its collapsed state after the bias voltage is removed. One suitable material is polydimethyl siloxane (PDMS or RTV rubber). The RTV material is cast over the CMUT while the bias voltage $V_B$ holds the membrane in its desired collapsed state. After the RTV polymerizes and is sufficiently stiff to physically retain the membrane in its precollapsed state, the bias voltage can be removed and does not need to be reapplied until the device is biased for operation. Preferably the lens material is bonded to the areas around each membrane of the CMUT array. Other materials which may be suitable for the lens 40 include urethane rubber, vinyl plastisols, and thermoplastic elastomers.

By physically retaining the membrane in its precollapsed state, no bias is necessary to maintain the precollapsed condition until the operating bias is applied during use of the device. This means that the CMUT can be operated at lower voltages, which is advantageous for small, portable ultrasound systems. Furthermore, adverse effects due to variability in manufacturing and material characteristics, such as variation in membrane size, stiffness or cavity depth from lot to lot can be eliminated. These variabilities may mean that more or less bias voltage is needed to bring the CMUT to its precollapsed state. The bias voltage is adjusted accordingly to the desired degree of collapse, and then the lens material holds the membrane in this state. Thus, each CMUT array can be set up for the same performance characteristics or its coupling customized even in the presence of these tolerance variations. Greater uniformity of the probes in terms of characteristics such as operating voltage range, acoustic impedance, capacitance, and coupling coefficient can be achieved.

Figure 8:
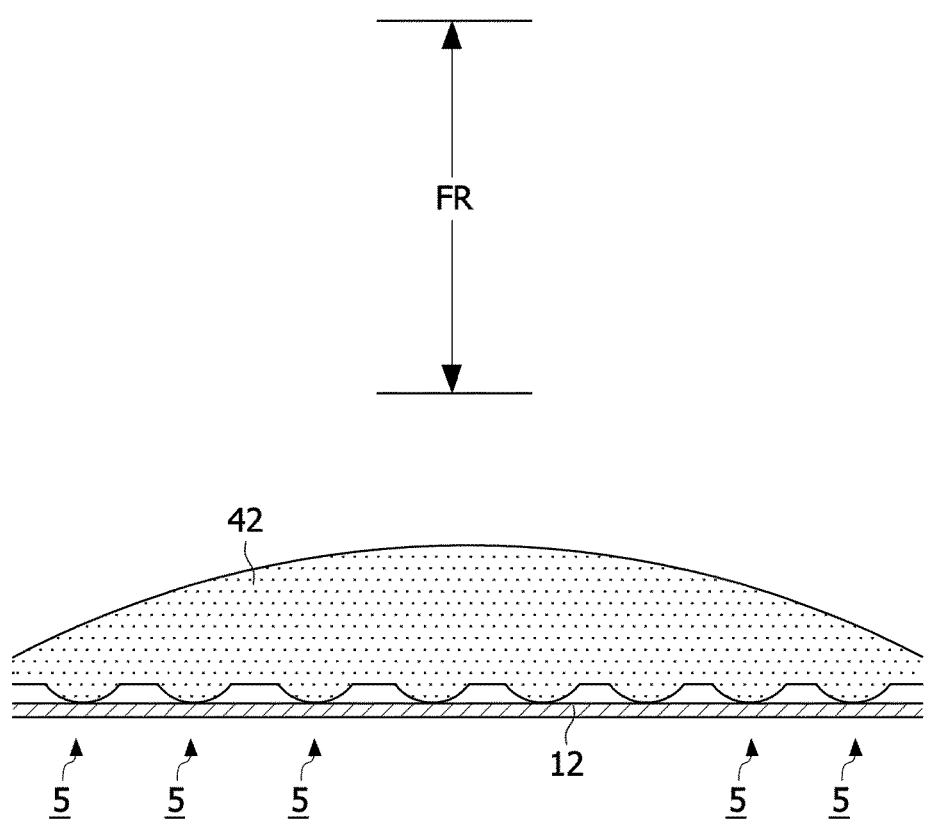
FIG. 8 illustrates an array of CMUT cells held in the precollapsed state by a lens providing a focal characteristic for the array.

FIG. 8 illustrates an example of an implementation of the present invention where an array of precollapsed CMUTs 5 are held in the precollapsed state by a lens 42. This lens material exhibits a slower speed of sound than does the human body, thereby focusing the array toward a central focal region. Without a focusing lens the individual CMUTs would all be focused straight ahead and the array as a whole is focused at infinity. When such an array is operated to focus it in a desired focal range, a considerable range of delay is needed to effect the desired focusing. A focusing lens 42 as shown in FIG. 8 can act to give the array a nominal focus within a desired focal range such as the focal range FR shown in front of the CMUT array of FIG. 8. With the lens providing this initial focus, the range of delay needed to change the focus to specific points or regions within the focal range is decreased. By placing the lens focal point within the focal range of interest, the delay requirements of the beamformer can be reduced by a factor of two as compared with that required for an unfocused plane wave array. When the delay requirements of the beamformer which operates the array are reduced, the beamformer will generally be less expensive and difficult to design and manufacture.

In an exemplary constructed array of CMUT transducer cells, the membrane of each CMUT is 50 ⊠ m in diameter or width, the cavity is 0.33 ⊠ m deep, and the CMUT is 1-5 ⊠ m thick. The lens may be 500-1000 ⊠ m thick and exhibit a stiffness of 1 megaPascal.

Figure 1:
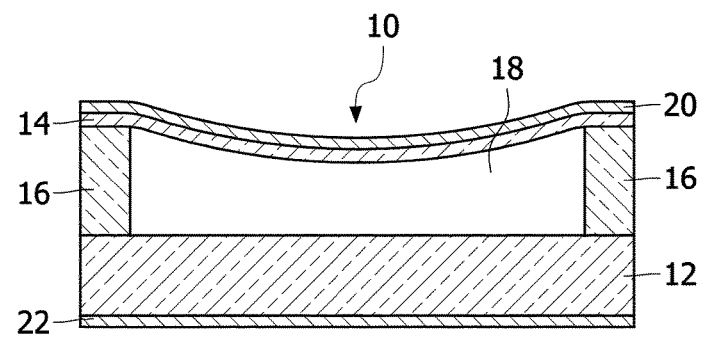
FIG. 1 is a cross-sectional view of a typical CMUT transducer cell.
Figure 2:
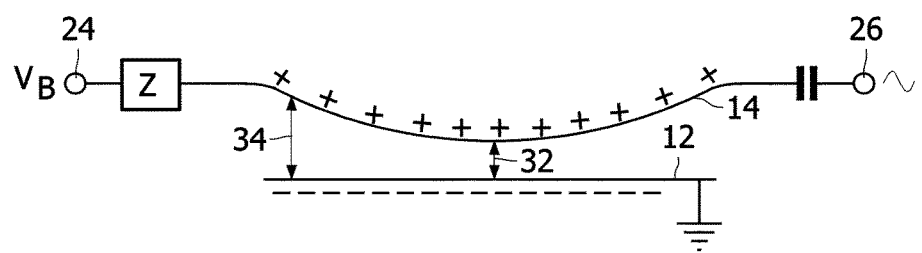
FIG. 2 is a schematic illustration of the electrical properties of a typical CMUT cell.

The coupling coefficient of a CMUT in the precollapsed state is improved and can be varied with lower voltage than is the case for the CMUT when operating in an uncollapsed state (FIGS. 1 and 2).

Figure 9:
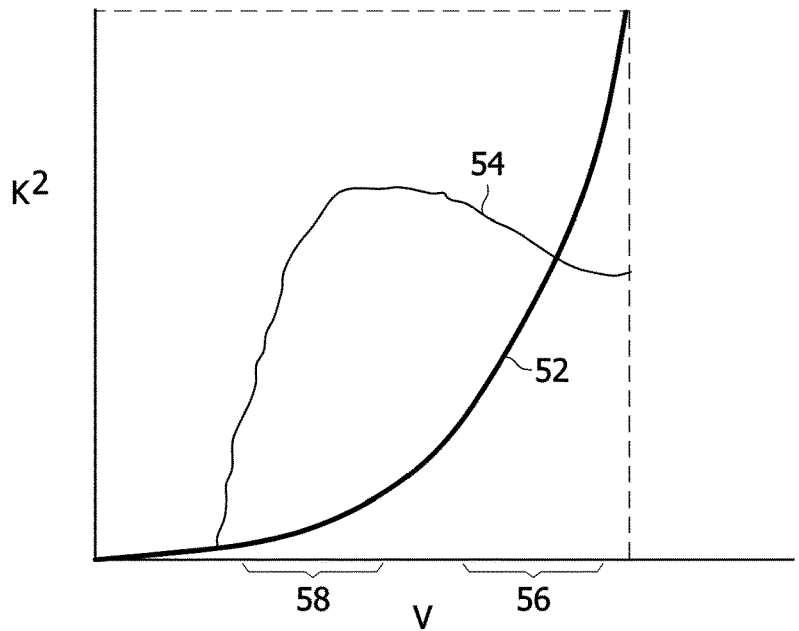
FIG. 9 illustrates the variation of the coupling coefficients of precollapsed and uncollapsed CMUT cells with voltage.

The coupling coefficient of a CMUT cell is a measure of the efficiency of energy storage by the device and is calculated as:

$$k^2 = 1 - \frac{C_s}{C_T}$$

where $$C_s = \frac{Q}{V}$$

and $$C_T = \frac{dQ}{dV}$$

and Q is charge and V is voltage. Hence, a higher coupling coefficient is a desirable attribute of an ultrasound transducer, be it a standard piezoelectric transducer or a CMUT array transducer. In the case of a CMUT cell, the variation of the coupling coefficient $k^2$ with voltage rises in the uncollapsed state as the voltage increases from zero, as shown by curve 52 in FIG. 9. As the membrane is biased to more closely approach the floor of the CMUT cell as shown at 32 in FIG. 2, the coupling coefficient $k^2$ changes more rapidly. Hence, the uncollapsed mode CMUT is operated at this higher voltage range 56 as shown in FIG. 9. In the precollapsed state, however, the variation of $k^2$ with voltage is as shown by curve 54. Here, the variation of $k^2$ is steepest at the lower voltages, in the range indicated by the lower voltage range bracket 58.

Figure 10:
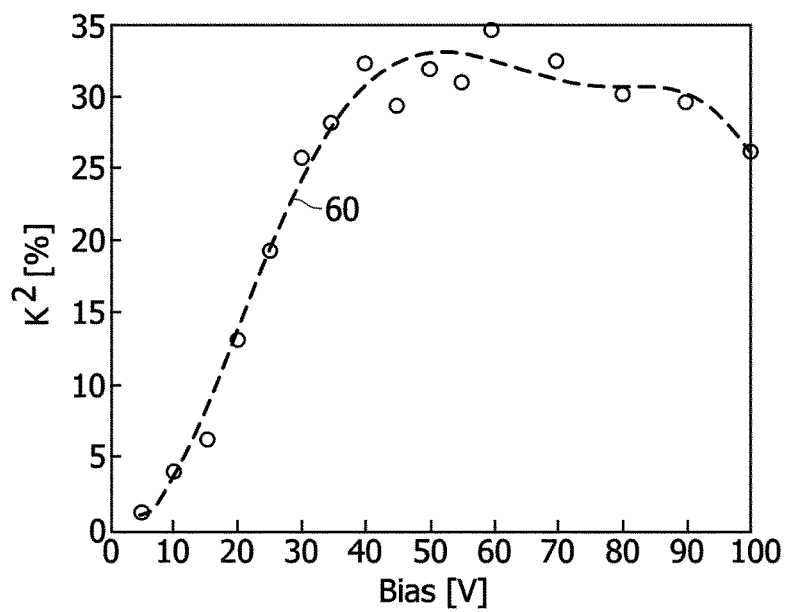
FIG. 10 illustrates the variation of the measured coupling coefficient of a constructed embodiment of the present invention with voltage.

When the applied voltage to the CMUT electrodes is increased over the uncollapsed region of operation into the collapsed region, then back again, the coupling coefficient variation will exhibit a hysteresis effect. Essentially, $k^2$ will increase along curve 52 as the voltage increases and, when the voltage is decreased after collapse, the coupling coefficient will decrease back along curve 54. This hysteresis shows why it is desirable to operate entirely in one mode or the other. When a precollapsed CMUT is operated entirely in its precollapsed state it will not have the hysteresis problem, as shown by the curve 60 in FIG. 10. The curve 10 is drawn along the path of actual measurements of the coupling coefficient changes of a constructed CMUT cell as the voltage was changed. The measurement values are indicated by the small circles along the curve 60. This demonstrates the absence of hysteresis when a CMUT cell or array of the present invention are operated continuously in the precollapsed state.

As previously mentioned, coupling coefficients can be measured for all varieties of ultrasound transducers, and the greater the coupling coefficient, the better the performance of the transducer probe. A typical PZT transducer probe will exhibit an effective coupling coefficient $k^2_{E\!f\!f}$ (which considers only the resonance mode of interest) of 0.42. A higher performance material, single crystal piezoelectric, as described in U.S. Pat. No. 6,465,937 (Chen et al.), will exhibit an effective coupling coefficient of about 0.65. Precollapsed CMUT cells of the present invention can be produced with coupling coefficients in the same range at that of the best single crystal array probes, and calculations indicate that even higher coupling coefficients may be possible.

Other variations will readily occur to those skilled in the art. For instance, the lens material does not have to retain the membrane in a fully precollapsed state. The lens could act to hold the membrane only partially collapsed toward the floor of the CMUT, and a small bias voltage used to bring the membrane to a fully collapsed state. In other words, the fully collapsed state can be effected in part by a retention member such as the lens material, and in part by a bias voltage. As used herein the term "collapsed" or "precollapsed" can mean that the membrane is in contact with the floor of the CMUT cavity, or only partially distended toward the floor.

The CMUT transducer arrays of the present invention are suitable for use in both diagnostic and therapeutic ultrasound probes. CMUT arrays of several centimeters in diameter may find use in high intensity focused ultrasound (HIFU) probes. CMUT transducers of the present invention may be used in both external (transthoracic) and indwelling (catheter) ultrasound probes. As previously mentioned, CMUT arrays of the present invention are particularly desirable for concurrent fabrication with the microelectronics needed to operate the probe, as for instance a CMOS process that is used to produce both the CMUT array and its microbeamformer on the same or on bonded substrates.

What is claimed is:

1. An array of CMUT transducer cells comprising at least one CMUT transducer cell comprising:
    a substrate;
    a second electrode attached to the substrate;
    a movable membrane formed in spaced relationship to the second electrode to form a cavity having a top and a floor;
    a first electrode attached to the movable membrane; and
    a retention member overlaying the movable membrane when the movable membrane is collapsed to a precollapsed state by application of pressure or a bias voltage, wherein the movable membrane comprises a curvature in the precollapsed state, the retention member comprising a protrusion having a curved shape that is directly in continuous contact with the first electrode and the movable membrane at the curvature of the movable membrane so as to retain the movable membrane in its precollapsed state in the absence of the applied pressure or bias voltage such that a portion of the movable membrane is continually in contact with the floor of the cavity in the precollapsed state,
    wherein the first electrode is attached to the movable membrane at the curvature of the movable membrane.

2. The CMUT transducer cell of claim 1, wherein the retention member comprises polydimethyl siloxane, PDMS, RTV rubber, urethane, vinyl plastisol, or a thermoplastic elastomer.

3. The CMUT transducer cell of claim 1, wherein the retention member is cast over the CMUT transducer cell while the movable membrane is brought to a precollapsed state by a bias voltage.

4. The CMUT transducer cell of claim 1, wherein the retention member is cast over the CMUT transducer cell while the movable membrane is brought to a precollapsed state by application of pressure to the movable membrane.

5. The CMUT transducer cell of claim 4, wherein the pressure is atmospheric pressure.

6. The CMUT transducer cell of claim 1, further comprising: at least one additional CMUT transducer cells as described in claim 1, wherein a plurality of CMUT transducer cells comprises a transducer array, wherein the retention member further comprises an acoustic lens formed over the array of CMUT transducer cells.

7. The CMUT transducer array of claim 6, wherein the acoustic lens provides the array with a fixed focus within a field of interest which is less than of an unfocused plane wave.

8. The CMUT transducer array of claim 6, wherein the transducer array is incorporated in a diagnostic ultrasound probe; and wherein the ultrasound probe further comprises an electronic circuit coupled to the transducer array for operating the array.

9. The CMUT transducer array of claim 8, wherein the electronic circuit further comprises a microbeamformer circuit.

10. The CMUT transducer array of claim 9, wherein the transducer array and the microbeamformer circuit are located on the substrate.

11. The CMUT transducer array of claim 6, wherein the transducer array is formed by a CMOS-compatible semiconductor process; wherein the transducer array is incorporated in a therapeutic ultrasound probe; and wherein the ultrasound probe further comprises an electronic circuit coupled to the transducer array for operating the array, wherein the electronic circuit is formed by a CMOS-compatible semiconductor process.

12. A CMUT transducer cell comprising:
a substrate;
a second electrode attached to the substrate;
a movable membrane formed in spaced relationship to the second electrode to form a cavity having a top and a floor;
a first electrode attached to the movable membrane;
a retention member overlaying the movable membrane, wherein the movable membrane comprises a curvature, the retention member comprising a protrusion having a curved shape that is directly in continuous contact with the first electrode and the movable membrane at the curvature of the movable membrane so as to retain the movable membrane in its precollapsed state in an absence of applied pressure or bias voltage, wherein the precollapsed state comprises a portion of the movable membrane continually in contact with the floor of the cavity; and
a voltage source coupled to the transducer cell and configured to apply a bias voltage applied to the first and second electrodes, wherein the first electrode is attached to the movable membrane at the curvature of the movable membrane.

13. The CMUT transducer cell of claim 1, wherein the second electrode is insulated on a side facing the cavity.

14. The CMUT transducer cell of claim 1, wherein the second electrode is insulated with an oxide-nitride-oxide dielectric layer.

15. The CMUT transducer cell of claim 1, wherein the cavity is a cylindrically-shaped cavity.

16. The CMUT transducer cell of claim 15, wherein the first electrode comprises a ring-shaped electrode positioned above the cylindrically-shaped cavity.

17. The CMUT transducer cell of claim 12, wherein the second electrode is insulated on a side facing the cavity.

18. The CMUT transducer cell of claim 12, wherein the second electrode is insulated with an oxide-nitride-oxide dielectric layer.

19. The CMUT transducer cell of claim 12, wherein the cavity is a cylindrically-shaped cavity.

20. The CMUT transducer cell of claim 19, wherein the first electrode comprises a ring-shaped electrode positioned above the cylindrically-shaped cavity.

* * * * *